United States Patent [19]

Beck et al.

[11] Patent Number: 4,567,138
[45] Date of Patent: Jan. 28, 1986

[54] METHOD FOR DETERMINING γ-GLUTAMYLTRANSFERASE ACTIVITY AND KITS CONTAINING A NOVEL SUBSTRATE SOLUTION FOR USE THEREIN

[75] Inventors: James P. Beck, Newport Beach; Carlos E. Luna, Placentia, both of Calif.

[73] Assignee: Beckman Instruments, Inc., Fullerton, Calif.

[21] Appl. No.: 644,647

[22] Filed: Aug. 27, 1984

Related U.S. Application Data

[63] Continuation of Ser. No. 413,042, Aug. 30, 1982, abandoned.

[51] Int. Cl.[4] ............................................. C12Q 1/48
[52] U.S. Cl. ....................................... 435/15; 435/810
[58] Field of Search ................... 435/15, 24, 188, 193, 435/810

[56] References Cited

U.S. PATENT DOCUMENTS 3,892,631  7/1975  Carroll .................................. 435/24
3,979,447  9/1976  Bernt et al. ........................... 435/15
4,372,874  2/1983  Modrovich ........................... 435/15

*Primary Examiner*—Esther M. Kepplinger
*Attorney, Agent, or Firm*—W. H. May; A. Grant; R. S. Frieman

[57] ABSTRACT

A substrate solution comprising (a) a substrate selected from a group consisting of salts of L-γ-glutamyl-p-nitroanilide and L-γ-glutamyl-3-carboxy-p-nitroanilide; and (b) a polyol selected from a group consisting of alkyl polyols containing 2 to 10 carbon atoms and 2 to 10 hydroxy groups and polyethylene glycol having an average molecular weight of from about 200 to about 600.

Also, a kit for the determination of γ-glutamyltransferase activity of the type comprising (a) a buffered medium comprising a buffer and a γ-glutamyl residue acceptor; and (b) a substrate solution; the buffered medium and substrate solution being adapted such that preselected aliquots thereof can react in the presence of γ-glutamyltransferase to produce an absorbing cleavage product. The kit is characterized in that the substrate solution is as described above.

In addition, a method for determining γ-glutamyltransferase acitivity of the type comprising (a) contacting in any preselected order an aliquot of a buffered medium comprising a buffer and a γ-glutamyl residue acceptor, an aliquot of a substrate solution, and an aliquot of a sample to be assayed to thereby form a cleavage product; and (b) measuring the absorbance of said cleavage product. The method is characterized in that the substrate solution is as described above.

20 Claims, No Drawings

METHOD FOR DETERMINING γ-GLUTAMYLTRANSFERASE ACTIVITY AND KITS CONTAINING A NOVEL SUBSTRATE SOLUTION FOR USE THEREIN

This is a continuation of application Ser. No. 413,042, filed Aug. 30, 1982, now abandoned.

BACKGROUND OF THE INVENTION

1. Field of the Invention

This invention relates to a method for determining γ-glutamyltransferase activity as well as to a kit containing a novel substrate solution for use therein.

2. Description of the Prior Art

γ-glutamyltransferase [(γ-glutamyl)-peptide:amino acid γ-glutamyltransferase (EC 2.3.2.2)], discovered in 1950 by Hanes et al. (1, 2), catalyzes the transfer of the γ-glutamyl group from a γ-glutamyl peptide to an amino acid or another peptide.

Although γ-glutamyltransferase is widely distributed in human organs, an increase in its activity in serum is almost specifically an indicator of diseases of the hepatobiliary track or of hepatic involvement in the primary elements (3-7).

For determination of γ-glutamyltransferase activity, L-γ-glutamyl-p-nitroanilide (8) is at present almost invariably used as a substrate, because it allows a direct reaction rate measurement without deproteinization or any chemical treatment of the cleavage product, p-nitroanaline. Recently, a more soluble derivative of L-γ-glutamyl-p-nitroanilide, namely, L-γ-glutamyl-3-carboxy-p-nitroanilide has been described as an alternative substrate in the γ-glutamyltransferase assay (9).

Prior art solutions of both L-γ-glutamyl-3-carboxy-p-nitroanilide and L-γ-glutamyl-p-nitroanilide suffer from stability and solubility problems in their presently employed aqueous environments. For example, the relatively short shelf-life of aqueous solutions of both L-γ-glutamyl-3-carboxy-p-nitroanilide and L-γ-glutamyl-p-nitroanilide have necessitated the freeze-drying thereof to prolong the shelf-life of these products. To reconstitute the freeze-dried product requires one to place it in water and heat the resulting mixture to up to about 50° C. This reconstitution step is time consuming, causes greater variations in the resulting reagent, as well as a loss of substrate. In addition, the freeze-drying procedure itself creates larger lot-to-lot variations.

Accordingly, it would be very advantageous to develop a novel substrate solution for use in the assay of γ-glutamyltransferase wherein such substrate solution comprises a substrate dissolved in a matrix such that the resulting substrate solution possesses increased stability and overcomes the solubility problems present in prior art.

SUMMARY OF THE INVENTION

In accordance with the present invention, there is provided a stabilized novel substrate solution for use in an assay of γ-glutamyltransferase. More particularly, the present invention encompasses a substrate solution comprising (a) a substrate selected from a group consisting L-γ-glutamyl-p-nitroanilide salts and L-γ-glutamyl-3-carboxy-p-nitroanilide salts; and (b) a polyol selected from the group consisting of alkyl polyols having 2 to 10 carbon atoms and 2 to 10 hydroxy groups and polyethylene glycol having an average molecular weight of from about 200 to about 600.

In addition, the instant invention encompasses a kit for the determination of γ-glutamyltransferase activity. The kit of the instant invention is of the type comprising (a) a buffered medium comprising a buffer and an acceptor for γ-glutamyl residue; and (b) a substrate solution. The buffered medium and substrate solution are adapted such that preselected aliquots thereof can react in the presence of γ-glutamyltransferase to produce an absorbing cleavage product. The kit of the instant invention is characterized in that the above described novel substrate solution is employed therein.

Furthermore, the instant invention also encompasses a method for determining γ-glutamyltransferase activity. The method of the instant invention is of the type comprising (a) contacting in any preselected order an aliquot of a buffered medium comprising a buffer and a γ-glutamyl residue acceptor, an aliquot of a substrate solution, and an aliquot of a sample to be assayed to thereby form a cleavage product and (b) measuring the absorbance of the cleavage product. The method of the instant invention is characterized in that the abovedescribed novel substrate solution is employed therein.

DESCRIPTION OF THE PREFERRED EMBODIMENTS

The novel substrate solution of the instant invention comprises a substrate and a polyol. Virtually any salt of L-γ-glutamyl-p-nitroanilide and L-γ-glutamyl-3-carboxy-4-nitroanilide can be employed as the substrate in the instant invention. Preferably, the substrate is selected from a group consisting of L-γ-glutamyl-p-nitroanilide hydrohalide and L-γ-glutamyl-3-carboxy-4-nitroanilide monoammonium salts. More preferably, the substrate is selected from the group consisting of the hydrochloride, hydrobromide, and hydroiodide salts of L-γ-glutamyl-p-nitroanilide. L-γ-glutamyl-p-nitroanlilide hydrochloride salt is the substrate of choice.

The substrate solution of the present invention can comprise from about 25 to about 250 mmol/L substrate. Preferably, the composition of the instant invention comprises from about 40 to about 100 mmol/L substrate. Optimally, the composition comprises about 50 mmol/L substrate.

The polyol employed in the substrate solution of the instant invention is selected from a group consisting of alkyl polyols containing from 2 to 10 carbon atoms and from 2 to 10 hydroxy groups and polyethylene glycol having an average molecular weight of from about 200 to about 600. Preferably, the polyol is selected from the group consisting of alkyl polyols containing from 2 to 5 carbon atoms and from 2 to 4 hydroxyl groups and polyethylene glycol having an average molecular weight of from about 200 to about 400. More preferably, the polyol is selected from the group consisting of glycerol, ethylene glycol, propylene glycol, 1,3-propanediol, butylene glycol, pentanediol, polyethylene glycol 200, and polyethylene glycol 300. Ethylene glycol, propylene glycol, polyethylene glycol 200, and polyethylene glycol 300 are the polyols of choice for use in the substrate solution of the instant invention.

The substrate solution of the instant invention is preferably an anhydrous system. However, a water content of no greater than 10%, preferably no greater than 5%, v/v is acceptable. Accordingly, the substrate solution of the instant invention optionally further comprises up to 20% v/v of an inert hydroscopic solid. More preferably, the substrate solution of the instant invention further comprises up to 5% v/v of the inert hydroscopic solid. The function of the optional inert hydroscopic solid is to achieve the preferred anhydrous embodiment of the substrate solution of the instant invention. The hydroscopic solid must be inert, an efficient water absorber, and of neutral or alkaline pH. The solid is preferably a high area hydroscopic agent such as a natural or synthetic molecular sieve having a particle size of from about 2 to about 16 mesh. The amount of surface area is important since the material acts to absorb water into the pores.

Molecular sieves are zeolites whose atoms are arranged in crystal lattice in such a way that there is a large number of small cavities interconnected by smaller openings or pores of precisely uniform size. Normally, these cavities contain water molecules, but upon heating under vacuum, this water is driven off without any change in the remaining crystal lattice. The network of cavities and pores may occupy 50% of the total volume of the crystals. Molecular sieves have a strong tendency to reabsorb water, and other small molecular weight liquids.

A few natural zeolites exhibit molecular sieve characteristics to a limited degree. Synthetic zeolites are available in several sizes (pore openings 3, 4 and 10 Angstrom units in diameter) with high capacity for absorption and regeneration even when used at elevated temperatures.

In general, the substrate solution of the instant invention can be made by dissolving a hydrohalide salt of L-$\gamma$-glutamyl-p-nitroanilide in a polyol, preferably an anhydrous polyol, at room temperature.

An alternate method to prepare the substrate solution is to add L-$\gamma$-glutamyl-p-nitroanilide free base to the polyol followed by the addition of a hydrohalide acid (in aqueous solution) to form a hydrohalide salt in situ. If one desires an anhydrous substrate solution, this method would require the addition of a molecular sieve to remove the added water.

The preferred technique for making the substrate solution of this invention entails the addition of L-$\gamma$-glutamyl-p-nitroanilide hydrochloride to anhydrous propylene glycol at room temperature with constant mixing to yield the desired solution.

Buffers which can be employed in the buffering medium of the kit of this invention include, but are not limited to, tris(hydroxymethyl)amino methane and any other buffer capable of maintaining the desired pH, preferably about pH 8.1$\pm$0.2, and which does not interfere in the recovery of $\gamma$-glutamyltransferase activity. The preferred buffer is tris(hydroxymethyl)amino methane.

Suitable $\gamma$-glutamyl residue acceptors include, but are not limited to, glycyglycine and S-methyl-L-cysteine. The preferred $\gamma$-glutamyl residue acceptor is glycyglycine.

A working reagent can be prepared by mixing an aliquot of the substrate solution with an aliquot of the buffered medium. Preferably, the working reagent is prepared by adding about one part of the substrate solution to about ten parts of the buffered medium and mixing the resulting solution.

The substrate solution and buffered medium should be formulated such that after mixing an aliquot of the substrate solution with an aliquot of the buffered medium in a ratio of from about 1:5 to about 1:50 to form the working reagent, the concentration of substrate in the working reagent is from about 1 to 10 mmol/L.

Although the sample to total volume ratio can vary, a 1:21 ratio has been found very satisfactory.

The following examples are provided for the purpose of further illustration only and are not intended to be limitations on the enclosed invention.

EXAMPLE 1

A preferred $\gamma$-glutamyltransferase reagent kit has the following formulation:

| Buffered Medium | Preferred | More Preferred | Optimal |
|---|---|---|---|
| Constituents | | | |
| Tris(hydroxymethyl)-aminomethane, m molar | 90–110 | 95–105 | 100 |
| Glycylglycine, m molar | 150–180 | 160–170 | 165 |
| Magnesium chloride, hexahydrate, m molar | 79–97 | 83–93 | 88 |
| Sodium azide | 0.8%–1.2% | 0.9%–1.1% | 1% |
| Sodium hydroxide as needed to adjust pH to: | 8.1 ± 0.2 | 8.1 ± 0.5 | 8.1 ± 0.1 |
| Purified water | Q.S.* to make desired volume | | |
| Substrate Solution | | | |
| Propylene glycol, anhydrous | Q.S. to make desired volume | | |
| $\gamma$-L-glutamyl-p-nitroanilide hydrochloride, m molar | 45–55 | 47–53 | 50 |

*Q.S. denotes a sufficient quantity

EXAMPLE 2

Various control and patient sera samples were assayed on a centrifugal fast analyzer in a correlation study employing the optimal $\gamma$-glutamyltransferase reagent kit of Example 1 and a commercially available $\gamma$-glutamyltransferase reagent kit and the results obtained therefrom are set forth in Table I.

TABLE I

| Sample | Commercial Kit (X) | $\gamma$-Glutamyltransferase Kit Without Scope of Invention (Y) |
|---|---|---|
| | IU/L | |
| Decision TM 1 | 20 | 17 |
| Decision TM 2 | 55 | 51 |
| Decision TM 3 | 114 | 108 |
| Linearity Control 1 | 17 | 14 |
| Linearity Control 2 | 35 | 32 |
| Linearity Control 3 | 64 | 62 |
| Linearity Control 4 | 123 | 120 |
| Linearity Control 5 | 240 | 238 |
| Linearity Control 6 | 357 | 354 |
| Linearity Control 7 | 485 | 480 |
| Linearity Control 8 | 592 | 589 |
| Patient Serum 1 | 9 | 8 |
| Patient Serum 2 | 34 | 31 |
| Patient Serum 3 | 21 | 20 |
| Patient Serum 4 | 26 | 25 |
| Patient Serum 5 | 21 | 20 |
| Patient Serum 6 | 25 | 23 |
| Patient Serum 7 | 10 | 10 |
| Patient Serum 8 | 26 | 27 |
| Patient Serum 9 | 57 | 58 |
| Patient Serum 10 | 81 | 84 |
| Patient Serum 11 | 19 | 21 |
| Patient Serum 12 | 24 | 24 |
| Patient Serum 13 | 22 | 26 |

The data set forth in Table I gives a correlation of $Y = 0.993X - 0.5 IU$ and a correlation coefficient (r) of 0.999. Accordingly, this data indicates that the results obtained via a $\gamma$-glutamyltransferase reagent within the scope of this invention correlate well with those obtained with a commercially available kit.

EXAMPLE 3

Stability Study

A fresh reagent within the scope of this invention and having a formulation as set forth in the "optimal" column of Example 1 was used to value assign a lot of Decision ™ controls and an in-house series of linearity control materials. These value assignments are set forth in Table II.

The fresh reagent was then packaged and incubated at 41° C. for 2 days in order to approximate one year storage at 5° C.

After the second day at 41° C., the reagent was then divided into two sets. One set was then stored at an incubation temperature of 30° C. and the other set was then stored at an incubation temperature of 37° C. Aliquots from both sets were periodically taken and employed in an γ-glutamyltransferase assay. The results obtained are also set forth in Table II.

TABLE II

| Sample | Value Assigned ±S.D.* | After 2 days @41° C. | day at 30° C. | | | day at 37° C. | | |
|---|---|---|---|---|---|---|---|---|
| | | | 1 | 2 | 3 | 1 | 2 | 3 |
| Decision 1 | 19.7 ± 1.8 | 21.9 | 19.1 | 20.0 | 21.7 | 19.6 | 23.9 | 20.0 |
| Decision 2 | 53.5 ± 1.9 | 55.0 | 52.5 | 53.8 | 55.6 | 53.7 | 52.9 | 50.7 |
| Decision 3 | 111 ± 1.8 | 113 | 111 | 111 | 111 | 110 | 106 | 104 |
| Linearity 1 Control | 15.7 ± 1.8 | 19.0 | 16.8 | 17.4 | 19.3 | 18.9 | 21.9 | 16.6 |
| Linearity 2 Control | 34.3 ± 2.1 | 37.5 | 35.3 | 36.4 | 37.1 | 36.1 | 38.6 | 30.0 |
| Linearity 3 Control | 64.5 ± 1.6 | 67.0 | 67.0 | 65.0 | 67.0 | 67.0 | 64.0 | 61.4 |
| Linearity 4 Control | 125 ± 3.6 | 126 | 125 | 122 | 125 | 122 | 121 | 116 |
| Linearity 5 Control | 245 ± 3.5 | 233 | 244 | 239 | 242 | 242 | 238 | 235 |
| Linearity 6 Control | 362 ± 3.5 | 361 | 361 | 351 | 356 | 355 | 354 | 339 |
| Linearity 7 Control | 488 ± 3.5 | 479 | 477 | 468 | 479 | 477 | 475 | 463 |
| Linearity 8 Control | 597 ± 4.1 | 582 | 587 | 583 | 581 | 583 | 582 | 570 |
| Absorbance @405 nm | 0.549 | 0.566 | 0.595 | 0.583 | 0.615 | 0.591 | 0.626 | 0.493 |

*S.D. denotes standard deviation

The data set forth in Table II indicates the good stability of the γ-glutamyltransferase reagents of the instant invention.

Based on this disclosure, many other modifications and ramifications will naturally suggest themselves to those skilled in the art. These are intended to be comprehended as within the scope of this invention.

Bibliography

1. Hanes et al., *Nature*, 166:288-299 (1950).
2. Hanes et al., *Biochem. J.*, 51:25-35 (1952).
3. Kokot et al., *Z. Gesamte Inn. Med. Ihre Grenzgeb*, 18:851-856 (1963).
4. Rutenburg et al., *Gastroenterology*, 45:43-48 (1963).
5. Zein, *Lancet*, ii:748-750 (1970).
6. Mayr, *Wien. Klin. Wochenschr.*, 85:83-87 (1973).
7. Schmidt et al., *Dtsch. Med. Wochenschr.*, 98:1572-1578 (1973).
8. Orlowski et al., *Biochim. Biophys. Acta*, 73:679-681 (1963).
9. Persijn et al., *LAB.*, 3:108 (1976). Abstract.

The embodiments of the invention in which an exclusive property or privilege is claimed are defined as follows:

1. A substantially anhydrous substrate solution comprising:
    (a) a substrate selected from the group consisting of salts of L-γ-glutamyl-p-nitroanilide; and
    (b) a polyol selected from the group consisting of alkyl polyols containing 2 to 10 carbon atoms and 2 to 10 hydroxy groups and polyethylene glycol having an average molecular weight of from about 200 to about 600 in an amount sufficient to solubilize and stabilize said substrate.

2. The substrate solution of claim 1 wherein:
    (a) said substrate is selected from the group consisting of L-γ-glutamyl-p-nitroanilide hydrohalide salts; and
    (b) said polyol is selected from the group consisting of alkyl polyols containing from 2 to 5 carbon atoms and from 2 to 4 hydroxyl groups and polyethylene glycol having an average molecular weight of from about 200 to about 400.

3. The substrate solution of claim 1 wherein:
    (a) said substrate is selected from the group consisting of L-γ-glutamyl-p-nitroanilide hydrochloride, L-γ-glutamyl-p-nitroanilide hydrobromide, L-γ-glutamyl-p-nitroanilide hydroiodide salts; and
    (b) said polyol is selected from the group consisting of glycerol, ethylene glycol, propylene glycol, 1,3-propanediol, butylene glycol, pentanediol, polyethylene glycol 200, and polyethylene glycol 300.

4. The substrate solution of claim 1 wherein:
    (a) said substrate is L-γ-glutamyl-p-nitroanilide hydrochloride salt; and
    (b) said polyol is selected from the group consisting of ethylene glycol, propylene glycol, polyethylene glycol 200, and polyethylene glycol 300.

5. The substrate solution of claim 4 comprising from about 25 to about 250 mmol/L substrate.

6. The substrate solution of claim 4 comprising from about 40 to about 100 mmol/L substrate.

7. The substrate solution of claim 4 comprising about 50 mmol/L substrate.

8. A kit for the determination of γ-glutamyltransferase activity of the type comprising:
  (a) a buffered medium comprising a buffer and a γ-glutamyl residue acceptor; and
  (b) a substrate solution;
said buffered medium and substrate solution being adapted such that preselected aliquots thereof can react in the presence of γ-glutamyltransferase to produce an absorbing cleavage product, characterized in that said substrate solution is substantially anhydrous and comprises:
  (a) a substrate selected from the group consisting of salts of L-γ-glutamyl-p-nitroanilide; and
  (b) a polyol selected from a group consisting of alkyl polyols containing 2 to 10 carbon atoms and 2 to 10 hydroxy groups and polyethylene glycol having an average molecular weight of from about 200 to about 600 in an amount sufficient to solubilize and stabilize said substrate.

9. The kit of claim 8 wherein:
  (a) said substrate is selected from the group consisting of L-γ-glutamyl-p-nitroanilide hydrohalide salts; and
  (b) said polyol is selected from the group consisting of alkyl polyols containing from 2 to 5 carbon atoms and from 2 to 4 hydroxyl groups and polyethylene glycol having an average molecular weight of from about 200 to about 400.

10. The kit of claim 8 wherein:
  (a) said substrate is selected from the group consisting of L-γ-glutamyl-p-nitroanilide hydrochloride, L-γ-gluamyl-p-nitroanilide hydrobromide, and L-γ-glutamyl-p-nitroanilide hydroiodide salts; and
  (b) said polyol is selected from the group consisting of glycerol, ethylene glycol, propylene glycol, 1,3-propanediol, butylene glycol, pentanediol, polyethylene glycol 200, and polyethylene glycol 300.

11. The kit of claim 8 wherein:
  (a) said substrate is L-γ-glutamyl-p-nitroanilide hydrochloride salt; and
  (b) said polyol is selected from the group consisting of ethylene glycol, propylene glycol, polyethylene glycol 200, and polyethylene glycol 300.

12. The kit of claim 8 wherein said substrate solution comprises from about 25 to about 250 mmol/L substrate.

13. The kit of claim 8 wherein said substrate solution comprises from about 40 to about 100 mmol/L substrate.

14. The kit of claim 8 wherein said substrate solution comprises about 50 mmol/L substrate.

15. A method for determining γ-glutamyltransferase activity of the type comprising:
  (a) contacting in any preselected order an aliquot of a buffered medium comprising a buffer and a γ-glutamyl residue acceptor, an aliquot of a substrate solution, and an aliquot of a sample to be assayed to thereby form a cleavage product; and
  (b) measuring the absorbance of said cleavage product; characterized in that said substrate solution is substantially anhydrous and comprises:
  (a) a substrate selected from the group consisting of L-γ-glutamyl-p-nitroanilide salts; and
  (b) a polyol selected from the group consisting of alkyl polyols containing 2 to 10 carbon atoms and 2 to 10 hydroxy groups and polyethylene glycol having an average molecular weight of from about 200 to about 600 in an amount sufficient to solubilize and stabilize said substrate.

16. The method of claim 15 wherein:
  (a) said substrate is selected from the group consisting of L-γ-glutamyl-p-nitroanilide hydrohalide salts; and
  (b) said polyol is selected from the group consisting of alkyl polyols containing from 2 to 5 carbon atoms and from 2 to 4 hydroxyl groups and polyethylene glycol having an average molecule weight of from abou 200 to about 400.

17. The method of claim 15 wherein:
  (a) said substrate is selected from the group consisting of L-γ-glutamyl-p-nitroanilide hydrochloride, L-γ-glutamyl-p-nitroanilide hydrobromide, and L-γ-glutamyl-p-nitroanilide hydroiodide salts; and
  (b) said polyol is selected from the group consisting of glycerol, ethylene glycol, propylene glycol, 1,3-propanediol, butylene glycol, pentanediol, polyethylene glycol 200, and polyethylene glycol 300.

18. The method of claim 15 wherein:
  (a) said substrate is L-γ-glutamyl-p-nitroanilide hydrochloride salt; and
  (b) said polyol is selected from the group consisting of ethylene glycol, propylene glycol, polyethylene glycol 200, and polyethylene glycol 300.

19. The method of claim 18 wherein said substrate solution comprises from about 40 to about 100 mmol/L substrate.

20. The method of claim 18 wherein said substrate solution comprises about 50 mmol/L substrate.

* * * * *